United States Patent
Diez Garcia et al.

(10) Patent No.: US 9,834,763 B2
(45) Date of Patent: Dec. 5, 2017

(54) EXPRESSION OF RECOMBINANT BETA-XYLOSIDASE ENZYMES

(71) Applicant: Abengoa Bioenergia Nuevas Tecnologias, S.A., Seville (ES)

(72) Inventors: Bruno Diez Garcia, Seville (ES); Ana Gomez Rodriguez, Seville (ES); Jorge Gil Martinez, Seville (SE); Noelia Valbuena Crespo, Seville (ES); Antonio Javier Moreno Perez, Seville (ES); Rafael Duenas Sanchez, Seville (ES); Ana Maria Munoz Gonzalez, Seville (ES); Dolores Perez Gomez, Seville (ES); Lucia Martin Perez, Seville (ES); Sandra Gavalda Martin, Seville (ES); Laura Sanchez Zamorano, Seville (ES); Consolacion Alvarez Nunez, Seville (ES); Maria de los Angeles Bermudez Alcantara, Seville (ES); Pablo Gutierrez Gomez, Seville (ES); Ricardo Arjona Antolin, Seville (ES)

(73) Assignee: Abengoa Bioenergia Nuevas Tecnologias, S.A. (ES)

( * ) Notice: Subject to any disclaimer, the term of this patent is extended or adjusted under 35 U.S.C. 154(b) by 0 days.

(21) Appl. No.: 14/891,068

(22) PCT Filed: May 20, 2013

(86) PCT No.: PCT/ES2013/070318
§ 371 (c)(1),
(2) Date: Nov. 13, 2015

(87) PCT Pub. No.: WO2014/188012
PCT Pub. Date: Nov. 27, 2014

(65) Prior Publication Data
US 2016/0272956 A1 Sep. 22, 2016

(51) Int. Cl.
| | |
|---|---|
| *C12N 1/20* | (2006.01) |
| *C12N 9/42* | (2006.01) |
| *C12N 9/24* | (2006.01) |
| *C12P 19/14* | (2006.01) |
| *C12N 15/62* | (2006.01) |
| *C12P 7/06* | (2006.01) |
| *C12P 7/10* | (2006.01) |
| *C12P 19/02* | (2006.01) |
| *C12P 19/12* | (2006.01) |

(52) U.S. Cl.
CPC .......... *C12N 9/248* (2013.01); *C12N 15/625* (2013.01); *C12P 7/065* (2013.01); *C12P 7/10* (2013.01); *C12P 19/02* (2013.01); *C12P 19/12* (2013.01); *C12P 19/14* (2013.01); *C12Y 302/01037* (2013.01); *Y02E 50/16* (2013.01); *Y02E 50/17* (2013.01)

(58) Field of Classification Search
CPC ............................... C12P 19/14; C12N 9/2434
USPC ........................................ 435/99, 209, 252.3
See application file for complete search history.

(56) References Cited

U.S. PATENT DOCUMENTS

| | | |
|---|---|---|
| 7,399,627 B2 | 7/2008 | Emalfarb et al. |
| 7,794,962 B2 | 9/2010 | Emalfarb et al. |
| 2008/0194005 A1 | 8/2008 | Emalfarb et al. |
| 2014/0106408 A1* | 4/2014 | Mitchinson ............. C12P 19/02 435/99 |

FOREIGN PATENT DOCUMENTS

| | | |
|---|---|---|
| WO | 2008073914 A2 | 6/2008 |
| WO | 2012018691 A2 | 2/2012 |
| WO | 2012125937 A2 | 9/2012 |

OTHER PUBLICATIONS

K.B. Bastawde, "Xylan structure, microbial xylanases, and their mode of action", World Journal of Microbiology and Biotechnology 8, 1998, pp. 353-368.
National Renewable Energy Laboratory, Bioenergy, "Biomass Compositional Analysis Laboratory Procedures", 7 pages, (http://www.nrel.gov/bioenergy/biomass-compositional-analysis.html), accessed Nov. 10, 2016.
Parveen Kumar et al, "Methods of Pretreatment of Lignocellulosic Biomass for Efficient Hydrolysis and Biofuel Production", Ind. Eng. Chem. Res 2009, 48, pp. 3713-3729.
Q.A. Nguyen et al, "Dilute Acid Pretreatment of Softwoods", Applied Biochemistry and Biotechnology, vol. 70-72, 1998, 11 pages.

(Continued)

*Primary Examiner* — Tekchand Saidha
(74) *Attorney, Agent, or Firm* — Hayes Soloway PC

(57) ABSTRACT

The present invention relates to a *Myceliophthora thermophila* host cell which expresses a recombinant enzymes from *Fusarium oxysporum* with beta-xylosidase activity. The invention also refers to an enzymatic composition comprising the host cell of the invention and/or the recombinant enzyme with beta-xylosidase activity expressed by the host cell of the invention. The invention further relates to the use of the host cell of the invention, the recombinant enzyme with beta-xylosidase activity expressed by the host cell of the invention or the composition of the invention for the degradation of biomass and to a method of producing bioproducts, preferably bioethanol, which comprises the use of the host cell of the invention, the recombinant enzyme with beta-xylosidase activity expressed by the host cell of the invention or the composition of the invention.

7 Claims, 7 Drawing Sheets

(56) References Cited

OTHER PUBLICATIONS

Jan C. Verdoes et al, "A dedicated vector for efficient library construction and high throughput screening in the hyphal fungus Chrysosporium lucknowense", Industrial Biotechnology 3 (1), Spring 2007, pp. 47-58.
Hans Visser et al, "Development of a mature fungal technology and production platform for industrial enzymes based on a Myceliophthora thermophila isolate, previously known as Chrysosporium lucknowense C1", Industrial Biotechnology 7(3), Jun. 2011, pp. 214-223.
Segato et al., High-yield secretion of multiple client proteins in Aspergillus, Enzyme and Microbial Technology, Jul. 5, 2012, pp. 100-106, vol. 51, Issue 2, Elsevier, Inc., https://doi.org/10.1016/j.enzmictec.2012.04.008.

\* cited by examiner

EXPRESSION OF RECOMBINANT BETA-XYLOSIDASE ENZYMES

The invention relates to the field of bioproducts, preferably biofuels, and more particularly, to the expression of recombinant enzymes with beta-xylosidase activity in host cells and its use in the production of bioproducts, preferably bioethanol, from biomass.

BACKGROUND ART

Nowadays, many efforts are being made in order to obtain less expensive and renewable sources of fuel. Biofuels offer an attractive alternative to petroleum based fuels and can be obtained through the fermentation of monomeric sugars derived from starch or cellulose. However, current economics do not support the widespread use of biofuels due to the high cost of generating them.

Plant biomass provides a plentiful source of potential energy in form of sugars that can be utilized for numerous industrial and agricultural processes, and is therefore a significant renewable resource for the generation of fermentable sugars that can yield commercially valuable end-products, such as biofuel. However, the enormous energy potential of these carbohydrates is currently under-utilized because the sugars are locked in complex polymers and, hence, are not readily accessible for fermentation (WO2012018691A2).

Wood, agricultural residues, herbaceous crops, and municipal solid wastes have been considered as feedstocks for ethanol production. These materials primarily consist of cellulose, hemicellulose, and/or lignin. Once the cellulose is converted to glucose by means of an enzymatic hydrolytic process, the glucose is easily fermented by yeast into ethanol. Thus, the more amounts of complex sugars remaining at the end of the hydrolytic process the lower the yield of ethanol production at the end of the fermentation process. Therefore, one area of research aimed at decreasing costs and enhancing the yield of biofuel production processes is focus on the enhancement of the technical efficacy of the hydrolytic enzymes that can be used to generate fermentable sugars from biomass.

Due to the complexity of biomass, its conversion to monomer sugars involves the action of several different enzyme classes, which digest cellulose and hemicellulose, major polysaccharides comprised in cellulosic materials. After cellulose, hemicellulose is the second most abundant fraction available in nature. It is a storage polymer in seeds and it forms the structural component in cell walls of woody plants. The classification of these hemicellulose fractions depends on the types of sugar moieties present. The principal monomers present in most of the hemicelluloses are D-xylose, D-mannose, D-galactose and L-arabinose. Thus, hemicellulose includes xylan, mannan, galactan and arabinan as the main heteropolymers. Specifically, xylan contains 85 to 93% of D-xylose, a small amount of c-arabinose and traces of glucuronic acid residues. The main chain of xylan is composed of β-(1-4) linked β-xylopyranose residues, and several side chains have been described to be present. Among them, most usually found are xylopiranose, glucuronic acid and arabinofuranose linkages, as well as acetyl groups (Bastawde, 1992, *World Journal of Microbiology and Biotechnology* (8) 353-368).

The presence of lignin in biomass leads to a protective barrier that prevents proper enzymatic hydrolysis of glucan and xylan. Thus, a pretreatment process of the biomass is required for increasing the access of the enzymes to their substrates and consequent efficient hydrolysis. Pretreatment uses various techniques, including ammonia fiber explosion, chemical treatment and steam explosion at high temperatures to alter the structure of cellulosic biomass and make cellulose more accessible. Hemicellulose can be readily hydrolysed under moderate conditions, but much more extreme conditions are needed for cellulose hydrolysis. Therefore, the pretreated material (substrate for the enzymatic hydrolysis) usually contains a high concentration of xylose, whereas glucose content is rather low (Kumar et al, 2009. *Ind. Eng. Chem. Res.*, 48 (8), 3713-3729).

Single component enzymes have been shown to only partially digest cellulose and hemicellulose and thus the concerted action of different classes of enzymes is required to complete their conversion to monomeric sugars. Many more enzymes are required to digest hemicellulose to sugar monomers including xylanase, xylosidase, arabinofuranosidase, mannanase, galactosidase and glucuronidase. Non-glycosyl hydrolases such as acetyl xylan esterase and ferulic acid esterase may also be involved.

A large number of naturally-occurring organisms have been found to produce enzymatic hydrolysis of cellulosic materials to produce fermentable sugars. Organisms capable of carry out a complete cellulose and hemicellulose degradation, that subsequently allows an efficient fermentation, would greatly enhance the cost effectiveness of bioethanol production.

The hydrolytic efficiency of a multi-enzyme complex in the process of cellulosic saccharification (or hydrolysis) depends both on properties of the individual enzymes and the ratio of each enzyme within the complex. It is therefore desirable to generate cellulolytic enzymes expressing-microorganisms which improve the yield of cellulosic material degradation process, increasing the amount of released fermentable sugars and thus improving the yield of final biofuel production.

Thus, some efforts carried out in order to generate improved cellulolytic enzymes expressing-microorganisms have involved inserting a gene encoding the specific hydrolytic enzyme to be expressed under the control of strong expression signals, which leads to an increased stability of the transcribed mRNA or an increased number of copies of the gene in the produced organism (US20080194005A1).

A number of host cells used for heterologous gene expression, such as bacteria *Escherichia coli*, and methods of transformation have been disclosed in the prior art. In this context, also a number of fungal expression systems have been developed, for instance *Aspergillus niger, Aspergillus awamori, Aspergillus nidulans, Trichoderma reesei*. However, for various reasons many of these recombinant microorganisms have not found widespread acceptance or use. In general terms, the ideal host cell must fulfill a large number of criteria, such as, uses the medium efficiently, produces the polypeptide or protein of interest in high yield, should be capable of efficient secretion of the protein or polypeptide, allows a wide range of expression regulatory elements to be used thus ensuring ease of application and versatility, allows the use of easily selectable markers that are cheap to use, and produce stable transformants.

DESCRIPTION OF THE INVENTION

The present invention relates to the recombinant expression of a beta-xylosidase enzyme which comprises an amino acid sequence that is at least 70% identical to SEQ ID NO: 3, preferably the beta-xylosidase enzyme of SEQ ID NO: 3, in a host cell, more preferably in *Myceliophthora thermo-*

*phila*, even more preferably in *Myceliophthora thermophila* strain C1. Said recombinant expression leads to a cell with improved efficiency of hydrolysis of biomass into fermentable sugars, more particularly the degradation of xylan oligomers to xylose (see FIGS. 7 and 8), as compared with the wild type cell that does not express said recombinant beta-xylosidase, being thus useful in methods of producing bioproducts, preferably biofuel, from biomass.

The present invention represents a solution to the need to provide a microorganism that expresses a mixture of cellulolytic enzymes which improves the yield of biomass hydrolytic process or saccharification, increasing the amount of released fermentable sugars and thus improving the yield of bioproducts, preferably biofuel, obtained after the fermentative process.

An important percentage of xylose of constituent biomass polysaccharides is not released in the process of enzymatic hydrolysis of biomass. The host cell of the invention expresses a recombinant beta-xylosidase enzyme which is capable of degrading xylan oligomers to xylose. Thus, this host cell and the enzymatic cocktail produced by it are useful for the optimization of the hydrolysis step of biomass into fermentable sugars.

The inventors have demonstrated that the incorporation, and successful later expression, of a recombinant beta-xylosidase enzyme which comprises an amino acid sequence that is at least 70% identical to SEQ ID NO: 3, preferably the mature beta-xylosidase FoBxl from the fungus *Fusarium oxysporum* which consists of the amino acid sequence SEQ ID NO: 3, in a host cell, preferably *Myceliophthora thermophila*, enhances the concentration of released xylose from biomass when the transformed cell or the enzymatic cocktail produced by said cell is used in a process of hydrolysis of biomass. This represents an increase in the final concentration of fermentable sugars, and hence of the overall yield of bioproducts, preferably biofuel, production.

Therefore, a first aspect of the present invention is related to a host cell which expresses a recombinant beta-xylosidase enzyme which comprises an amino acid sequence that is at least 70% identical to SEQ ID NO: 3, from now on referred to as "host cell of the invention".

The term "β-xylosidase" refers to a protein that hydrolyses short 1,4-β-D-xylooligomers into xylose. The "recombinant β-xylosidase" of the invention is a beta-xylosidase enzyme which is naturally expressed in a microorganism other than the host cell of the invention, i. e. a heterologous β-xylosidase, the amino acid sequence of which has not been modified or has been modified preferably by means of one or more deletions, insertions, substitutions, etc.

In a preferred embodiment, the recombinant β-xylosidase is a naturally occurring beta-xylosidase derived from a microorganism other than the host cell of the invention, more preferably from a *Fusarium* cell, even more preferably from a *Fusarium oxysporum* cell.

The recombinant β-xylosidase referred to in the present invention comprises an amino acid sequence that is at least 70% identical to SEQ ID NO: 3. Recombinant β-xylosidases comprising amino acid sequences that are at least 70% identical to SEQ ID NO: 3 may be obtained from a filamentous fungal, such as, *Acremonium, Aspergillus, Aureobasidium, Cryptococcus, Gibberella, Filibasidium, Fusarium, Humicola, Magnaporthe, Mucor, Neocallimastix, Neurospora, Paecilomyces, Penicillium, Piromyces, Schizophyllum, Talaromyces, Thermoascus, Thielavia, Tolypocladium*, or *Trichoderma*. In a more preferred embodiment, the recombinant β-xylosidase is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium pseudograminearum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Gibberella zeae, Humicola insolens, Humicola lanuginosa, Mucor miehei, Neurospora crassa, Penicillium purpurogenum, Trichoderma harzianum, Trichoderma koningii, Trichoderma longibrachiatum, Trichoderma reesei*, or *Trichoderma viride* β-xylosidase.

In a more preferred embodiment, the recombinant beta-xylosidase enzyme comprises an amino acid sequence that is at least 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 3. Examples of beta-xylosidase enzymes comprising an amino acid sequence that is at least 70% identical to SEQ ID NO: 3 are the enzyme FG11468.1 from *Gibberella zeae* (Gene Bank Accession Number XP_391644.1) or the enzyme FPSE_09342 from *Fusarium pseudograminearum* (Gene Bank Accession Number EKJ70481.1).

In a more preferred embodiment, the recombinant beta-xylosidase enzyme comprises the amino acid sequence SEQ ID NO: 3. This SEQ ID NO: 3 corresponds to the mature beta-xylosidase enzyme from the fungus *F. oxysporum* named FoBxl. Examples of beta-xylosidase enzymes comprising the amino acid sequence SEQ ID NO: 3 are the polypeptide of SEQ ID NO: 2, which consists of the native signal peptide of the beta-xylosidase FoBxl of *F. oxysporum* corresponding to amino acids 1 to 20 of SEQ ID NO: 2 linked to SEQ ID NO: 3; or SEQ ID NO: 4, which consists of the signal peptide of glucoamylase from *Aspergillus niger* (glaA, accession number An03g06550) corresponding to amino acids 1 to 18 of SEQ ID NO: 4 linked to SEQ ID NO: 3. In an even more preferred embodiment, the recombinant beta-xylosidase enzyme which comprises the amino acid sequence SEQ ID NO: 3 is SEQ ID NO: 4. As it will be shown in examples below, the highest yield of released xylose and xylobiose during the hydrolytic process of biomass was obtained when the host cell of the invention expressed this SEQ ID NO: 4 (see FIGS. 7 and 8 and Table 1).

In other preferred embodiment, the recombinant beta-xylosidase enzyme consists of the amino acid sequence SEQ ID NO: 3.

The term "identity" refers to the ratio of nucleic or amino acid residues that are identical between two nucleic acid or amino acid sequences that are being compared. The degree of identity can be determined by the Clustal method, the Wilbur-Lipman method, the GAG program, including GAP, BLAST or BLASTN, EMBOSS Needle and FASTA. Furthermore, the Smith Waterman algorithm can be used in order to determine the degree of identity between two sequences.

The "host cell", as used herein, includes any cell type which is susceptible to transformation, transfection, transduction, and the like with a nucleic acid construct or expression vector comprising a polynucleotide encoding the recombinant beta-xylosidase enzyme referred to above. The choice of a host cell will to a large extend depend upon the gene encoding the polypeptide and its source. The host cell may be eukaryote, such as mammalian, insect, plant or fungal cell. In a preferred embodiment, the host cell is a filamentous fungal cell. Filamentous fungi are generally characterized by a mycelial wall composed of chitin, cellulose, glucan, chitosan, mannan, and other complex polysaccharides. In a more preferred embodiment, the filamentous fungal host cell is an *Acremonium, Aspergillus, Aureobasidium, Bjerkandera, Ceriporiopsis, Coprinus, Coriolus, Cryptococcus, Filibasidium, Fusarium, Gibberella, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell. In a most preferred embodiment, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium pseudograminearum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred embodiment, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Gibberella zeae, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell. In an even more preferred embodiment, the host cell of the invention is any strain of the species *Myceliophthora thermophila*. In an even more preferred embodiment, the host cell of the invention is *Myceliophthora thermophila* strain C1.

It will be understood that for the aforementioned species the invention encompasses both perfect and imperfect states, and other taxonomic equivalents, e. g. anamorphs, regardless of the species name by which they are known. Those skilled in the art will readily recognize the identity of appropriate equivalents. For instance, *Myceliophthora thermophila* is equivalent to *Chrysosporium lucknowense.*

When the recombinant beta-xylosidase enzyme comprises the amino acid sequence SEQ ID NO: 3 or consist of the amino acid sequence SEQ ID NO: 3, the host cell is not *Fusarium oxysporum.*

In an even more preferred embodiment, the host cell is *Myceliophthora thermophila*, more preferably *Myceliophthora thermophila* strain C1 and the recombinant beta-xylosidase expressed in it is selected from the list consisting of: SEQ ID NO: 2, SEQ ID NO: 3 or SEQ ID NO: 4, more preferably the recombinant beta-xylosidase is SEQ ID NO: 4 or SEQ ID NO: 3, even more preferably the recombinant beta-xylosidase is SEQ ID NO: 4.

The host cell of the invention comprises a nucleic acid sequence encoding a recombinant beta-xylosidase disclosed herein. Nucleic acid sequences encoding these recombinant beta-xylosidases can encode the mature polypeptide or a preprotein consisting of a signal peptide linked to the mature enzyme which will have to be subsequently processed. Nucleic acid sequences encoding beta-xylosidases can be included in a genetic construct, preferably in an expression vector. Said genetic construct may further comprise one or more regulatory sequences of gene expression, such as promoters, terminators, etc.

In accordance with the present invention, "nucleic acid sequence" or "polynucleotide" is a nucleic acid molecule (polynucleotide) that has been removed from its natural milieu (i.e., that has been subject to human manipulation) and can include DNA, RNA, or derivatives of either DNA or RNA, including cDNA. The nucleotide sequence of the present invention can be or not chemically or biochemically modified and can be artificially performed by means of cloning and selection methods or by sequencing.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for the expression of a coding sequence of the recombinant beta-xylosidase.

The term "control sequences" is defined herein to include all components which are necessary or advantageous for the expression of a polynucleotide encoding a recombinant beta-xylosidase of the present invention. Each control sequence may be native or foreign to the nucleotide sequence encoding the recombinant beta-xylosidase. Such control sequences include, but are not limited to, a leader, polyadenylation sequence, propeptide sequence, promoter, signal peptide sequence, and transcription terminator. At a minimum, the control sequences include a signal peptide sequence, preferably the amino acids 1 to 18 of SEQ ID NO: 4, and preferably a promoter, and transcriptional and translational stop signals. The control sequences may be provided with linkers for the purpose of introducing specific restriction sites facilitating ligation of the control sequences with the coding region of the nucleotide sequence encoding the recombinant beta-xylosidase. The term "operably linked" denotes herein a configuration in which a control sequence is placed at an appropriate position relative to the coding sequence of the polynucleotide sequence such that the control sequence directs the expression of the coding sequence of the recombinant beta-xylosidase.

The term "expression vector" is defined herein as a linear or circular DNA molecule that comprises a polynucleotide encoding the recombinant beta-xylosidase as disclosed herein, and which is operably linked to additional nucleotides that provide for its expression. Said vector comprising a polynucleotide encoding the recombinant beta-xylosidase is introduced into a host cell so that the vector is maintained as a chromosomal integrant or as a self-replicating extrachromosomal vector.

The nucleotide sequence encoding the beta-xylosidase described herein may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression. The expression vectors referred to in the present invention comprise a polynucleotide encoding the beta-xylosidase described herein, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the enzyme at such sites.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced.

The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors used in the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), pyr5, cysC (sulfate adenyltransferase), and trpC (anthranilate synthase), as well as equivalents thereof.

The vectors used in the present invention preferably contain an element(s) that permits integration of the vector into the host cell's genome or autonomous replication of the vector in the cell independent of the genome. For integration into the host cell genome, the vector may rely on the polynucleotide's sequence encoding the beta-xylosidase enzyme or any other element of the vector for integration into the genome by homologous or non homologous recombination. Alternatively, the vector may contain additional nucleotide sequences for directing integration by homologous recombination into the genome of the host cell at a precise location(s) in the chromosome(s).

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo. Examples of origins of replication useful in a filamentous fungal cell are AMA1 and ANSI.

More than one copy of a polynucleotide encoding the beta-xylosidase of the present invention may be inserted into the host cell to increase the production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected by cultivating the cells in the presence of the appropriate selectable agent. The procedures used to ligate the elements described above to construct the recombinant expression vectors referred to in the present invention are well known to one skilled in the art.

The term "expression" includes any step involved in the production of the recombinant beta-xylosidase including, but not limited to, transcription, post-transcriptional modification, translation, post-translational modification, and secretion.

The nucleic sequence included in the host cell of the invention may encode SEQ ID NO: 3, which is the mature beta-xylosidase from *Fusarium oxysporum*, or may encode a preprotein consisting of a signal peptide linked to said mature enzyme. This preprotein will have to be subsequently processed in the host cell in order to produce the mature beta-xylosidase enzyme. This preprotein could be, but is not limited to, either the polypeptide of SEQ ID NO: 2, which consists of the native signal peptide of the beta-xylosidase FoBxl of *F. oxysporum* corresponding to amino acids 1 to 20 of SEQ ID NO: 2 linked to SEQ ID NO: 3; or SEQ ID NO: 4, which consists of the signal peptide of glucoamylase gene from *A. niger* (glaA, accession number An03g06550) corresponding to amino acids 1 to 18 of SEQ ID NO: 4 linked to SEQ ID NO: 3. The preprotein SEQ ID NO: 2 is the native preprotein expressed in *Fusarium oxysporum*. Preferably, the host cell of the invention comprises a nucleic acid sequence encoding SEQ ID NO: 4, more preferably said nucleic acid sequence is SEQ ID NO: 5, and said cell therefore expresses the preprotein SEQ ID NO: 4 which will be processed into said cell in order to express the recombinant beta-xylosidase enzyme consisting of the amino acid sequence SEQ ID NO: 3.

Suitable nucleic acid sequences encoding a beta-xylosidase from *Fusarium oxysporum* are known in the art or can be designed based on the amino acid sequences given in the paragraph above. In a more preferred embodiment, the nucleic acid sequence encoding the polypeptide of SEQ ID NO: 2 is SEQ ID NO: 1. In another preferred embodiment, the nucleic acid sequence encoding the polypeptide of SEQ ID NO: 4 is SEQ ID NO: 5. In another preferred embodiment, the nucleic acid sequence encoding the polypeptide of SEQ ID NO: 3 is SEQ ID NO: 6.

The host cell of the invention expresses a functional recombinant beta-xylosidase enzyme and it is capable of secreting it to the extracellular medium. The term "functional" means that the expressed enzyme retains its capacity to hydrolyse xylan oligomers to xylose. This activity can be measured by means of any suitable method known in the state of the art to assess the beta-xylosidase activity, preferably by means of the method described below in examples of the present invention (measured on pNXP as substrate).

The expression of the beta-xylosidase in the host cell of the invention may be performed by means of any method known in the art, such as transformation of a suitable host cell with a nucleic acid sequence encoding the recombinant beta-xylosidase, or a genetic construction comprising said nucleic acid sequence, and cultivation of the transformed host cell under conditions which induce the expression of said nucleic acid sequence in order to obtained the secreted enzyme.

The host cell can be cultivated in a nutrient medium suitable for production of the recombinant beta-xylosidase using methods well known in the art. For example, the cell may be cultivated by shake flask cultivation, and small-scale or large-scale fermentation (including continuous, batch, fed-batch, or solid state fermentations) in laboratory or industrial bioreactor performed in a suitable medium and under conditions allowing the beta-xylosidase to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the beta-xylosidase is secreted into the nutrient medium, the beta-xylosidase can be recovered directly from the medium.

The recombinant beta-xylosidase expressed may be detected using methods known in the art that are specific for the polypeptides. These detection methods may include use of specific antibodies, formation of an enzyme product, or disappearance of an enzyme substrate.

The resulting beta-xylosidase may be recovered using methods known in the art. For example, the beta-xylosidase may be recovered from the nutrient medium by conventional procedures including, but not limited to, centrifugation, filtration, extraction, spray-drying, evaporation, or precipitation.

The beta-xylosidases produced in the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction, in order to obtain substantially pure beta-xylosidase that can be included in an enzymatic composition together with other cellulolytic enzymes.

Thus, a second aspect of the invention refers to a recombinant beta-xylosidase enzyme expressed by the host cell of the invention. Preferably, said recombinant beta-xylosidase enzyme consists of the amino acid sequence SEQ ID NO: 2, SEQ ID NO: 3 or SEQ ID NO: 4, more preferably SEQ ID NO: 4.

A third aspect of the invention refers to a composition comprising the recombinant beta-xylosidase enzyme produced by means of the host cell of the invention, preferably the enzyme consisting of SEQ ID NO: 3, and/or the host cell of the invention, hereinafter "composition of the invention". This composition of the invention may further comprise other enzymatic activities, such as aminopeptidase, amylase, carbohydrase, carboxypeptidase, catalase, cellulase, such as endoglucanases, beta-glucosidases and/or cellobiohydrolases; chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase, or any combination thereof. The additional enzyme(s) may be produced, for example, by a microorganism belonging to the genus *Aspergillus*, such as *Aspergillus aculeatus, Aspergillus awamori, Aspergillus fumigatus, Aspergillus foetidus, Aspergillus japonicus, Aspergillus nidulans, Aspergillus niger,* or *Aspergillus oryzae; Fusarium,* such as *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium pseudograminearum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Gibberella,* such as *Gibberella zeae; Humicola,* such as *Humicola insolens* or *Humicola lanuginosa; Trichoderma,* such as *Trichoderma harzianum, Trichoderma koningii, Trichoderma longibrachiatum, Trichoderma reesei,* or *Trichoderma viride;* or *Myceliophthora,* such as *Myceliophthora thermophila.*

In a preferred embodiment, the composition of the invention further comprises other cellulolytic enzymes. The term "cellulolytic enzymes" also known as "cellulases", refers to a category of enzymes capable of hydrolysing cellulose (β-1,4-glucan or β-D-glucosidic linkages) or hemicellulose to shorter oligosaccharides, cellobiose and/or glucose. Examples of cellulolytic enzymes are, but not limited to, endoglucanases, beta-glucosidases, cellobiohydrolases or endoxylanases. Thus, in a more preferred embodiment, these cellulolytic enzymes are selected from the list consisting of: endoglucanases, beta-glucosidases, cellobiohydrolases, endoxylanases or any combination thereof. These cellulolytic enzymes can derive from the host cell of the invention or other cellulolytic enzymes producers-microorganisms different from the host cell of the invention. Likewise, they can be naturally or recombinantly produced.

Preferably, the composition of the invention comprises the recombinant beta-xylosidase enzyme produced by means of the host cell of the invention, preferably the enzyme consisting of SEQ ID NO: 3, and other cellulolytic enzymes derived from the host cell of the invention. In a more preferred embodiment, the composition of the invention is an enzymatic mixture obtained by the host cell of the invention. In an even more preferred embodiment, the composition of the invention is an enzymatic mixture obtained by the host cell of the invention, preferably *M. thermophila,* wherein said cell comprises a nucleic acid sequence encoding the recombinant beta-xylosidase enzyme which consists of the amino acid sequence SEQ ID NO: 4.

The term "endoglucanase" or "EG" refers to a group of cellulase enzymes classified as E.C. 3.2.1.4. These enzymes hydrolyse internal β-1,4 glucosidic bonds of cellulose.

The term "cellobiohydrolase" refers to a protein that catalyzes the hydrolysis of cellulose to cellobiose via an exoglucanase activity, sequentially releasing molecules of cellobiose from the reducing or non-reducing ends of cellulose or cellooligosaccharides.

The term "beta-glucosidase" as used herein refers to an enzyme which catalyses the hydrolysis of a sugar dimer, including but not limited to cellobiose, with the release of a corresponding sugar monomer, used, but not limited, for the synthesis of ethanol. Beta-glucosidase enzyme acts upon β1→4 bonds linking two glucose or glucose-substituted molecules (i.e., the disaccharide cellobiose). It is an exocellulase with specificity for a variety of beta-D-glycoside substrates. It catalyzes the hydrolysis of terminal non-reducing residues in beta-D-glucosides with release of glucose.

The term "endoxylanase" refers to an enzyme which catalyzes the endohydrolysis of 1,4-beta-D-xylosidic linkages in xylanes.

The composition of the invention may be prepared in accordance with methods known in the art and may be in the form of a liquid or a dry composition. For instance, the composition may be in the form of a granulate or a microgranulate. The enzymes to be included in the composition may be stabilized in accordance with methods known in the art.

As stated above, the host cell of the invention expresses a recombinant beta-xylosidase enzyme, preferably the beta-xylosidase enzyme from *Fusarium oxysporum* of SEQ ID NO: 3, which is capable of degrading xylan oligomers to xylose when secreted to the extracellular medium. This host cell is capable of secrete this enzyme to the medium together with other native or recombinantly produced cellulolytic enzymes, being thus useful for the optimization of the hydrolysis step of biomass into fermentable sugars.

Therefore, a fourth aspect the invention relates to the use of the host cell of the invention, the recombinant beta-xylosidase enzyme produced by means of the host cell of the invention or the composition of the invention for the degradation of biomass.

The term "biomass" means the biodegradable fraction of products, waste and residues from biological origin from agriculture (including vegetal, such as crop residues, and animal substances), forestry (such as wood resources) and related industries including fisheries and aquaculture, as well as biodegradable fraction of industrial and municipal waste, such as municipal solid waste or wastepaper. In a preferred embodiment, the biomass is straw or organic fraction of municipal solid wastes. In a more preferred embodiment, the biomass is plant biomass, more preferably selected from the list consisting of: fermentable sugar-rich biomass, such as sugarcane, starchy biomass, for example, wheat grain, or corn straw.

The recombinant beta-xylosidase enzyme produced by means of the host cell of the invention, as well as the host cell or the composition of the present invention may be used in the production of monosaccharides, disaccharides, and polysaccharides as chemical or fermentation feedstocks from biomass for the production of ethanol, plastics, or other products or intermediates.

The host cell of the present invention may be used as a source of the polypeptide having beta-xylosidase activity, and other cellulolytic enzymes, in a fermentation process with the biomass.

The predominant polysaccharide in the primary cell wall of biomass is cellulose, the second most abundant is hemicellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually bind through hydrogen bonds to cellulose, as well as to other hemicelluloses, which helps stabilize the cell wall matrix. The recombinant beta-xylosidase enzymes produced by the host cell of the invention may be used in conjunction with the other cellulolytic enzymes to further degrade the cellulose component of the biomass substrate.

The degradation or hydrolysis of biomass into fermentable sugars, process also known as "saccharification", by means of the recombinant beta-xylosidase enzyme expressed by the host cell of the invention, the host cell of the invention or the composition of the invention can be followed by a fermentation process in which the obtained fermentable sugars are used in order to finally obtain a bioproduct such as bioethanol.

Thus, another preferred embodiment of this aspect of the invention refers to the use of the recombinant beta-xylosidase enzyme produced by means of the host cell of the invention, the host cell of the invention or the composition of the invention for the degradation of biomass in a bioproduct production process.

The term "bioproduct" or "bio-based products" refers to those materials, chemicals and energy derived from renewable biological resources. Examples of these bioproducts are, but not limited to, hydrocarbon compounds in their different forms, such as aliphatic (saturated, insaturated, cyclic) or aromatic, as alkanes, alkenes, alkines, cyclic forms of these compounds or aromatic hydrocarbons; oxygenated substances as alcohols, ethers, aldehydez, ketones or carboxylic acids; nitrogenated substances as amines, amides, nitrocompounds or nitriles; halogenated substances as halures. The term "bioproducts" includes also any combination of the compounds described above, compounds further derived from the compounds described above by any kind of physical, chemical or biological treatment, polymers from the compounds described above, compounds described above substituted by any functional group or element in one or more of their bounds and branched forms of the compounds described above.

Ethanol can be produced by enzymatic degradation of biomass and conversion of the released saccharides to ethanol. This kind of ethanol is often referred to as bioethanol. It can be used as a fuel additive or extender in blends of from less than 1% and up to 100% (a fuel substitute).

In a more preferred embodiment the bioproduct is biofuel. The term "biofuel" as used herein refers to a hydrocarbon, or a mixture thereof, which can be used as fuel and is obtained using fermentable biomass as starting material. Examples of biofuels include, but are not limit to, ethanol or bioethanol and biodiesel. In a more preferred embodiment, the biofuel is bioethanol.

The term "bioethanol" refers to an alcohol made by fermentation, mostly from fermentable biomass, such as carbohydrates produced in sugar or starch crops such as corn or sugarcane.

In a fifth aspect, the present invention refers to a method of producing fermentable sugars, hereinafter "first method of the invention", comprising:
  a) Incubating biomass, preferably pretreated biomass, with the host cell of the invention, the recombinant beta-xylosidase enzyme produced by means of the host cell of the invention or with the composition of the invention, and
  b) Recovering the fermentable sugars obtained after the incubation in step (a).

A pretreatment process of the biomass is often required for increasing the access of the enzymes to their substrates and consequent efficient hydrolysis. Pretreatment uses various techniques, including but not limited to ammonia fiber explosion, chemical treatment and steam explosion at high temperatures to alter the structure of cellulosic biomass and make cellulose more accessible. The use of the host cell of the invention, the recombinant beta-xylosidase enzyme produced by means of the host cell of the invention or the composition of the invention in the methods of the present invention is advantageous since high temperatures are not required in the pretreatment process of the biomass.

The term "fermentable sugar", as used herein, refers to simple sugars, such as glucose, xylose, arabinose, galactose, manose, rhanmose, sucrose or fructose, among others.

A sixth aspect of the present invention refers to a method of producing a bioproduct from biomass, hereinafter "second method of the invention", comprising:
  a) Incubating biomass, preferably pretreated biomass, with the host cell of the invention, the recombinant beta-xylosidase enzyme produced by means of the host cell of the invention or with the composition of the invention, b) Fermenting the fermentable sugars obtained after the incubation of step (a) with at least one fermenting microorganism, and c) Recovering the bioproduct obtained after the fermentation in step (b).

The term "fermenting or fermentation" as used herein, refers to a biological transformation process caused by the activity of some microorganisms in which sugars such as glucose, fructose, and sucrose are converted into ethanol. The microorganisms used therefore, are fermenting microorganisms, which have a fermentation capacity, such as yeast, preferably *S. cerevisiae*.

The term "recovery" as used herein, refers to the collection of fermentable sugars obtained after the incubation in step (a) of the first method of the invention or bioproduct obtained after fermentation of step (b) of the second method of the invention. The recovery may occur by any method known in the art, including mechanical or manual ones.

In a preferred embodiment of the second method of the invention, the bioproduct is biofuel, more preferably bioethanol.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings and sequence listing are provided by way of illustration and are not intended to be limiting of the present invention.

EXAMPLES

Example 1. Expression of Beta-Xylosidase FoBxl from *Fusarium oxysporum* (Strain Fo5176) in *M. thermophila* C1. Construction of the Expression Vector and Beta-Xylosidase Activity Analysis in *M. thermophila* Transformants

*M. thermophila* C1 has been described as a good quality transformation system for expressing and secreting heterologous proteins and polypeptides. The beta-xylosidase gene fobxl (FOXB_13892 Accession number: EGU75604) from *F. oxysporum* (Fo5176) was the target to express the enzyme and test its enzymatic quality in the present invention.

The fobxl cDNA sequence was synthesized in vitro after optimization, leading to remove the recognition sites for the most common restriction enzymes without altering the amino acid sequence. The cDNA nucleotide sequence of fobxl and the deduced amino acid sequence are shown in SEQ ID NO: 1 and SEQ ID NO: 2 respectively. The coding sequence is 1047 in length by including the stop codon. The encoded predicted protein is 348 amino acids long with a predicted molecular mass of 40 KDa and an isoelectric point of 9.02. Using the Signal IP program (Petersen et al., 2011, Signal IP 4.0, *Nature Methods*, 8:785-786), a signal peptide of 20 residues was predicted. The predicted mature protein (SEQ ID NO: 3) contains 328 amino acids with a predicted molecular mass of 37 KDa and an isoelectric point of 8.81.

Figure 1:
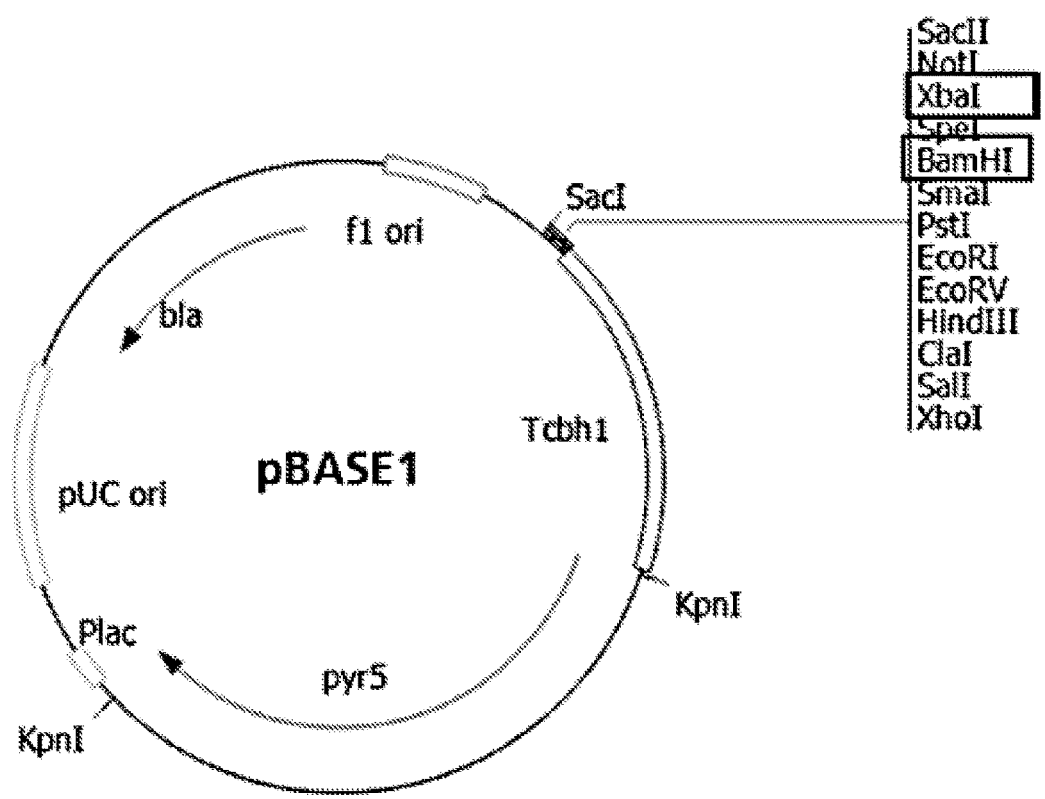
FIG. 1. Shows the vector named pBASE1. Expression vector with Tcbh1 as terminator sequence and pyr5 as selection marker. XbaI and BamHI were the restriction sites chosen for the cloning of Pcbh1-fobxl cassette.

The gene fobxl was in vitro synthesized together with the promoter sequence of cellobiohydrolase 1 gene (Pcbh1), corresponding with an upstream region of 1796 bp of the cellobiohydrolase 1 gene (cbh1, NCBI Accession number XP_003660789.1) of *M. thermophila* C1. This cassette (Pcbh1-fobxl) was synthesized in vitro including the sequence of the restriction enzymes XbaI and BamHI at the ends (5' and 3' ends, respectively) in order to be cloned into an expression vector named pBASE1. The expression vector pBASE1 also contained the terminator sequence of the cellobiohydrolase 1 gene from *Myceliophthora thermophila* C1 (Tcbh1, corresponding with a downstream region of 1014 bp of cbh1) and pyr5 gene (NCBI Accession number XP_003660657.1) from the same strain as selection marker. The pyr5 gene encodes for a functional orotate-phosphoribosyl transferase and its expression allows complementation of the uridine auxotrophy in the corresponding auxotrophic *M. thermophila* C1 host strain (pyr5). The expression vector pBASE1 is shown in FIG. 1.

Figure 2:
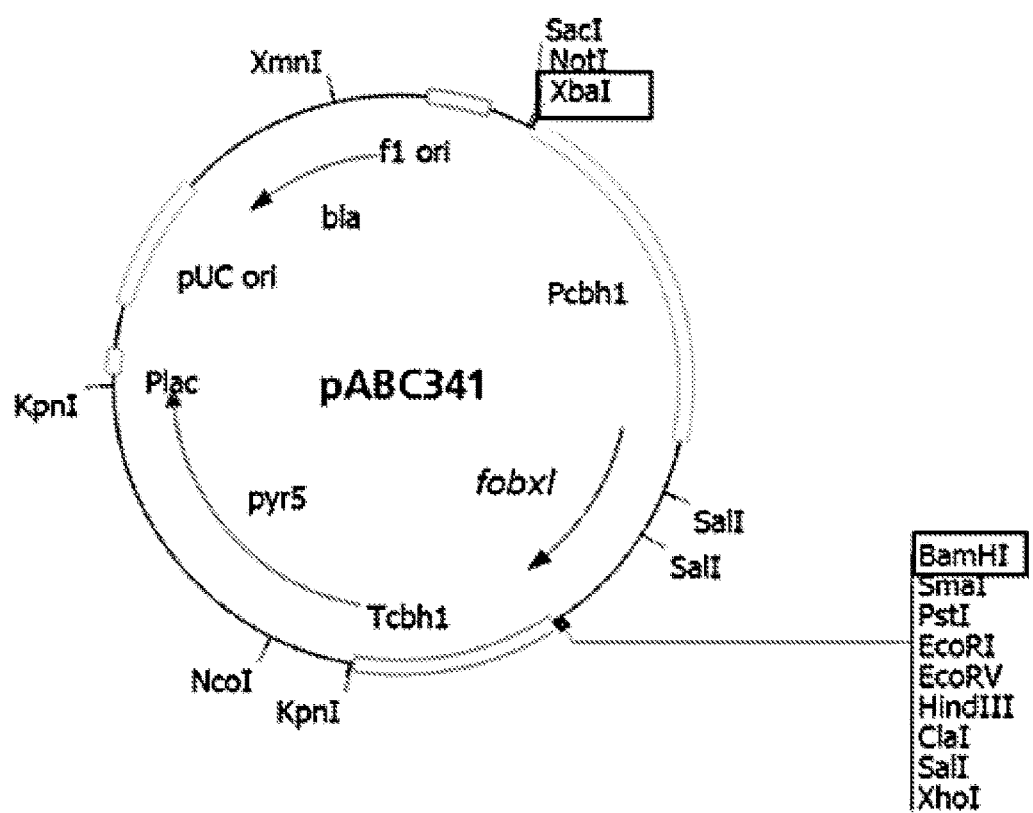
FIG. 2. Shows the vector named pABC341. Expression plasmid of native fobxl cDNA from *F. oxysporum*.

The cassette Pcbh1-fobxl was digested with the restriction enzymes XbaI and BamHI and cloned in the pBASE1 previously digested with the same restriction enzymes. The expression vector pBASE1 and the cassette Pcbh1-fobxl were ligated and the ligation product was transformed in XL1 Blue MRF Escherichia coli electro-competent cells following the protocol provided by the manufacturer (Stratagene). The recombinant plasmid obtained was named pABC341 and is shown in FIG. 2.

The pABC341 plasmid containing fobxl from *F. oxysporum* under Pcbh1 promoter sequence and pyr5 as selection marker, was transformed in the *M. thermophila* pyr5 (Verdoes et al., 2007, *Ind. Biotechnol.* 3 (1)), auxotrophic host strain previously used in other high-throughput screening in *M. thermophila*. The DNA was introduced in the host strain using a protoplast transformation method (U.S. Pat. No. 7,399,627B2). The transformants were plated out in agar plates with no uridine supplementation. After 5 days of incubation at 35° C., resulting prototrophic transformants (expressing pyr5 gene) were analysed.

The transformants obtained were inoculated in 96-well microtitter plates (MTPs) cultures to carry out a high throughput screening (U.S. Pat. No. 7,794,962B2). The aim of the screening was to identify beta-xylosidase activity in transformants expressing fobxl. Hydrolytic activity on p-nitrophenyl-beta-D-xylopyranoside (pNXP, Sigma N2132) as substrate was measured. Percentage of beta-xylosidase activity was measured by the release of p-nitrophenol (and consequent increase of $A_{410}$) in units per litter of culture (U/L). One unit of pNXP hydrolysing activity was defined as the amount of enzyme needed to release 1 µmol p-nitrophenol per minute. Beta-xylosidase activity of 50 µl of the culture supernatants of each transformant was assayed with 200 mg/L of pNXP for 10 minutes at 50° C. in a final volume of 100 µL. The reaction was stopped by adding 100 µL of carbonate 1M to the reaction mixtures. The hydrolytic capacity was measured by the release of p-nitrophenol (and consequent increase of $A_{410}$).

Figure 3:
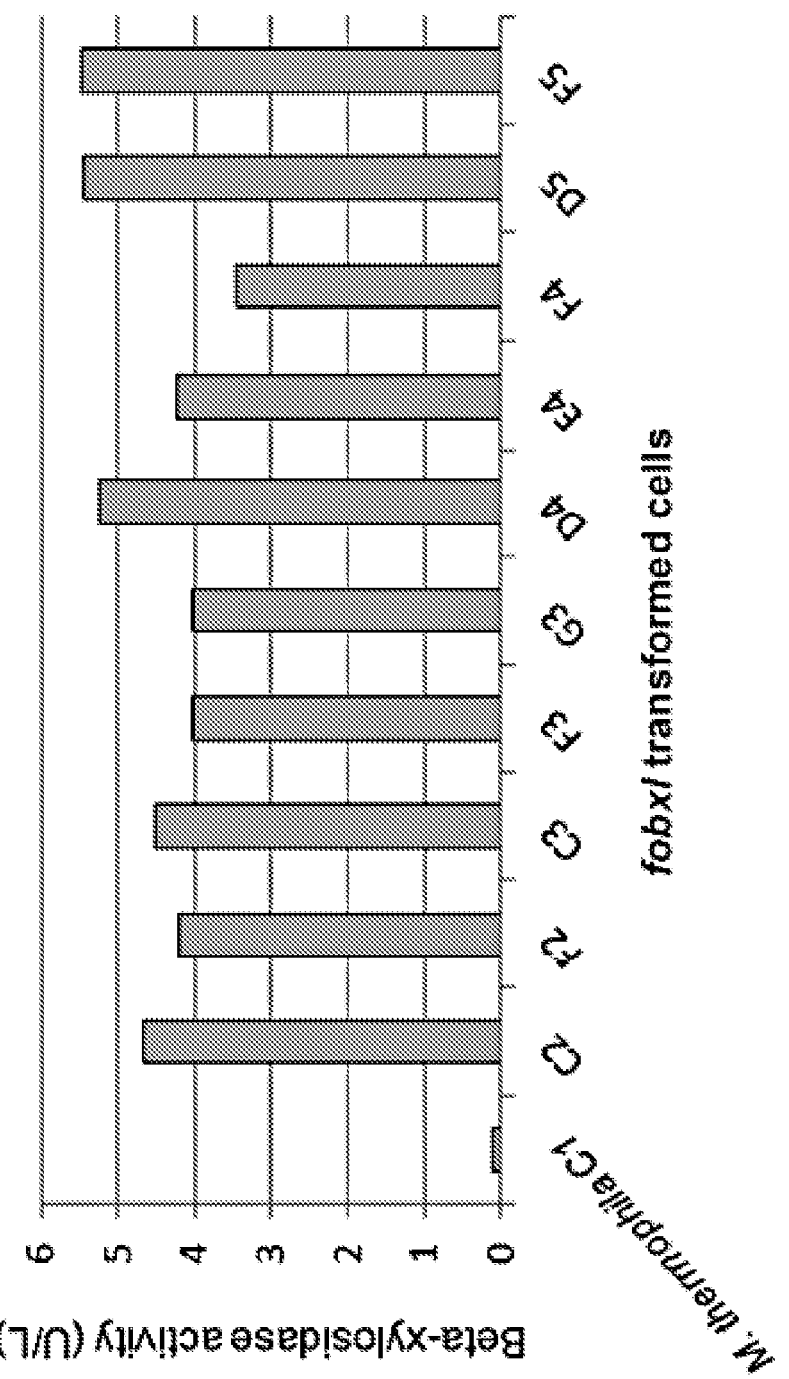
FIG. 3. Shows the beta-xylosidase activity (U/L) of some fobxl transformants analysed using pNXP as substrate.

Among the transformants tested, most of them showed an increase of beta-xylosidase activity using *M. thermophila* C1 as negative control. The results of beta-xylosidase activity are shown in FIG. 3. All the transformants with beta-xylosidase activity were confirmed in a second round test as defined in U.S. Pat. No. 7,794,962B2. Some of the positive transformants were confirmed with grown at flask scale production (Verdoes et al., 2007, *Ind. Biotechnol.* 3 (1); Visser et al., 2011, *Ind. Biotechnol.* 7 (3)) and beta-xylosidase activity was measured from culture supernatants.

Example 2. Genetic Fusion of Glucoamylase Signal Peptide from *A. niger* with Beta-Xylosidase FoBxl Mature Protein Sequence from *F. oxysporum*. Construction of an Expression Vector and Beta-Xylosidase Activity Analysis in *M. thermophila* Transformants The signal peptide from Fobxl native protein was exchanged to increase secretion of Fobxl mature protein in *M. thermophila*. Native signal peptide from Fobxl was substituted by the signal peptide of glucoamylase from *Aspergillus niger* (glaA, accession number An03g06550). Glucoamylase is a naturally highly secreted enzyme and its signal peptide was used to reach a highly secretion of the recombinant protein in the filamentous fungi.

For the native signal peptide substitution, the fragment of the fobxl gene encoding the mature protein (excluding sequence coding native signal peptide) was amplified by PCR using oligonucleotide 1 and 2. The oligonucleotide 1 (SEQ ID NO: 7) includes NdeI restriction site and the sequence coding glucoamylase signal peptide (SPGA). The oligonucleotide 2 (SEQ ID NO: 8) includes SmaI and BamHI restriction sites and includes the stop codon. The amplification from oligonucleotide 1 allows the genetic fusion of glucoamylase signal peptide and mature protein of Fobxl (SPGA-Fobxl).

Oligonucleotide 1 (SEQ ID NO: 7): NdeI restriction site is underlined. SPGA is framed. 5' end sequence of FoBxl mature protein is shadow texted.

5'-GATCCTCTTCCGTCCCAT ATGTCGTTCCGATCTCTTCTCGCCCTGAG

CGGCCTTGTCTGCTCGGGGTTGGCA CAAAACACTAATGACATTCCTCCGC

TGATCACCC-3'

Oligonucleotide 2 (SEQ ID NO: 8): SmaI and BamHI restriction sites are underlined. Stop codon is framed.

5'-CCTGCAGCCCGGGGGATCC CTA AGGACGGTGAAGCAAGATCTTGCC

GTTCTTGTC-3'

Figure 4:
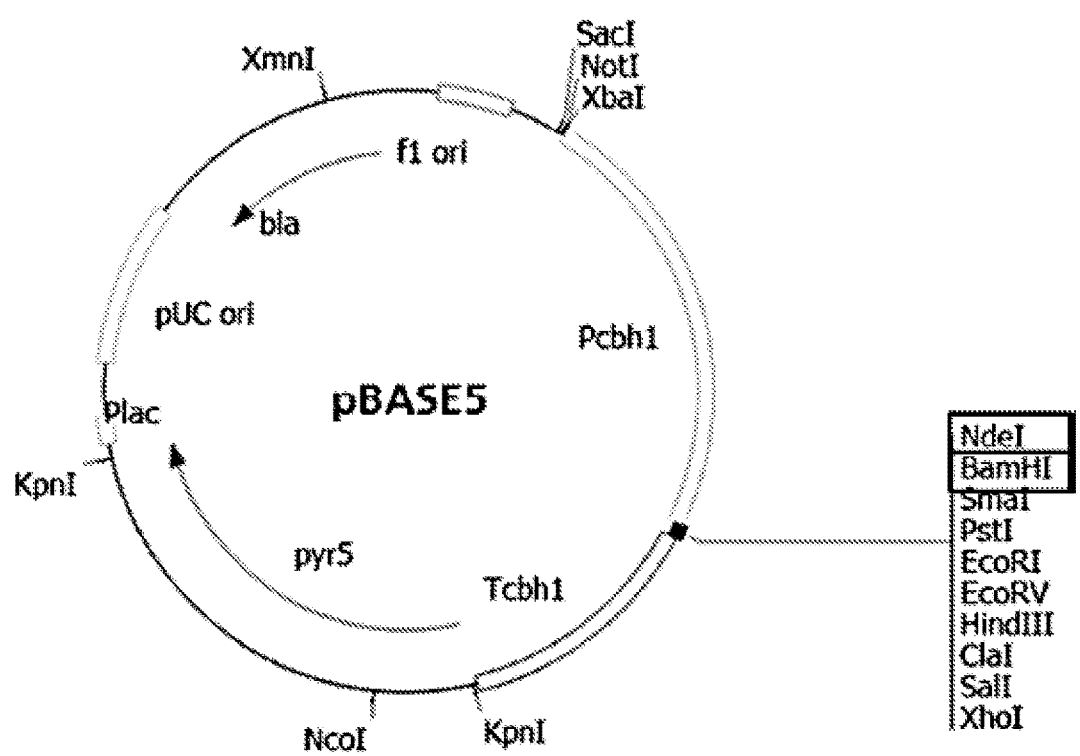
FIG. 4. Shows the vector named pBASE5. Expression vector with Pcbh1 as promoter sequence, Tcbh1 as terminator sequence and pyr5 as selection marker. NdeI and BamHI were the restriction sites chosen for the cloning of genetic fusion SPGA-fobxl.
Figure 5:
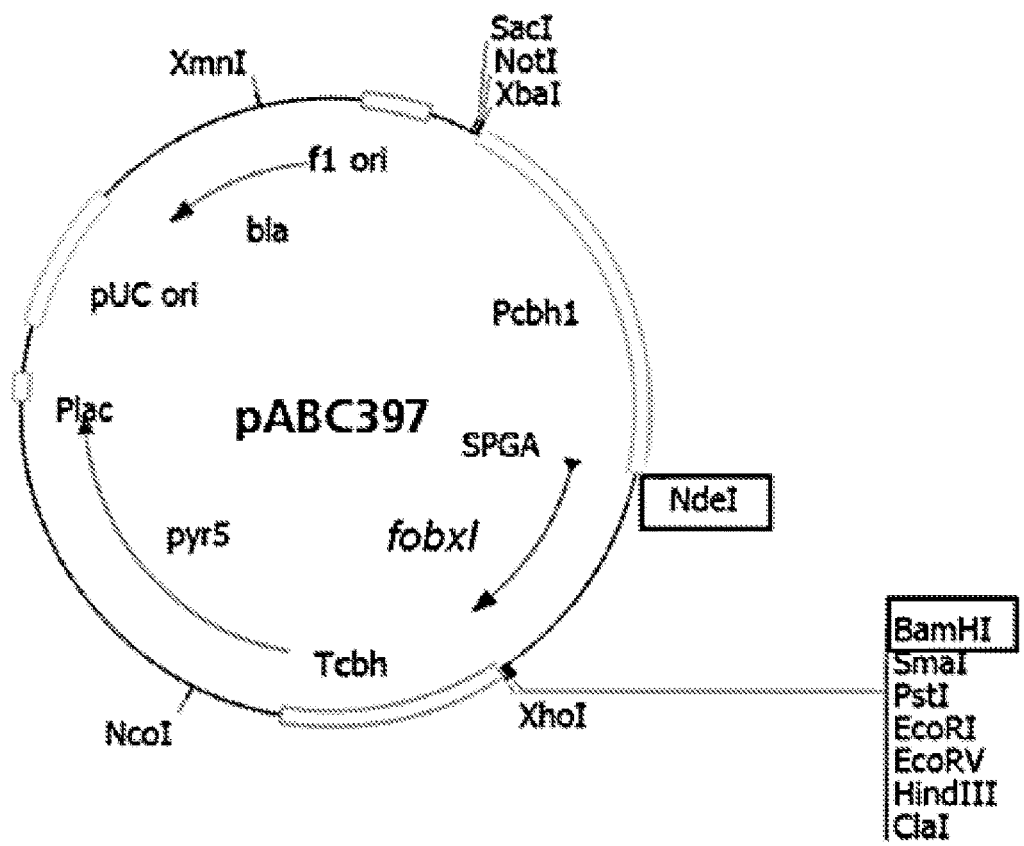
FIG. 5. Shows the vector named pABC397. Expression plasmid containing the genetic fusion SPGA-fobxl.

Amplification of genetic fusion SPGA-fobxl was performed using the oligonucleotides 1 and 2 using plasmid DNA pABC341 (previously described in Example 1) as target with iProof High-Fidelity DNA Polymerase (BioRad) and programmed for one cycle at 95° C. for 2 minutes and 30 cycles of 95° C. for 30 seconds, 60° C. for 30 seconds, 72° C. for 1 minute and one cycle of 72° C. for 10 minutes. The fragment of DNA amplified was digested with NdeI and BamHI restriction enzymes and cloned into pBASE5 previously digested with the same restriction enzymes (shown in FIG. 4). pBASE5 comes from pBASE1 (described in Example 1) where the promoter sequence Pcbh1 was cloned including NdeI restriction site. pBASE5 also contains Tchb1 as terminator sequence and pyr5 as selection marker (described in Example 1). The plasmid with SPGA-fobxl cloned under Pcbh1 was named pABC397 and is shown in FIG. 5.

The pABC397 plasmid containing the genetic fusion SPGA-fobxl under Pcbh1 promoter sequence and pyr5 as selection marker, was transformed in the *M. thermophila* pyr5- (Verdoes et al., 2007, *Ind. Biotechnol.* 3 (1)). The DNA was introduced in the host strain using a protoplast transformation method (U.S. Pat. No. 7,399,627B2). The transformants were plated out in agar plates with no uridine supplementation. After 5 days of incubation at 35° C., resulting prototrophic transformants (expressing pyr5 gene) were analysed.

High throughput screening of the transformants obtained was carried out as described in Example 1. The aim of the screening was to identify the beta-xylosidase activity in transformants expressing fobxl (as described in Example 1).

Figure 6:
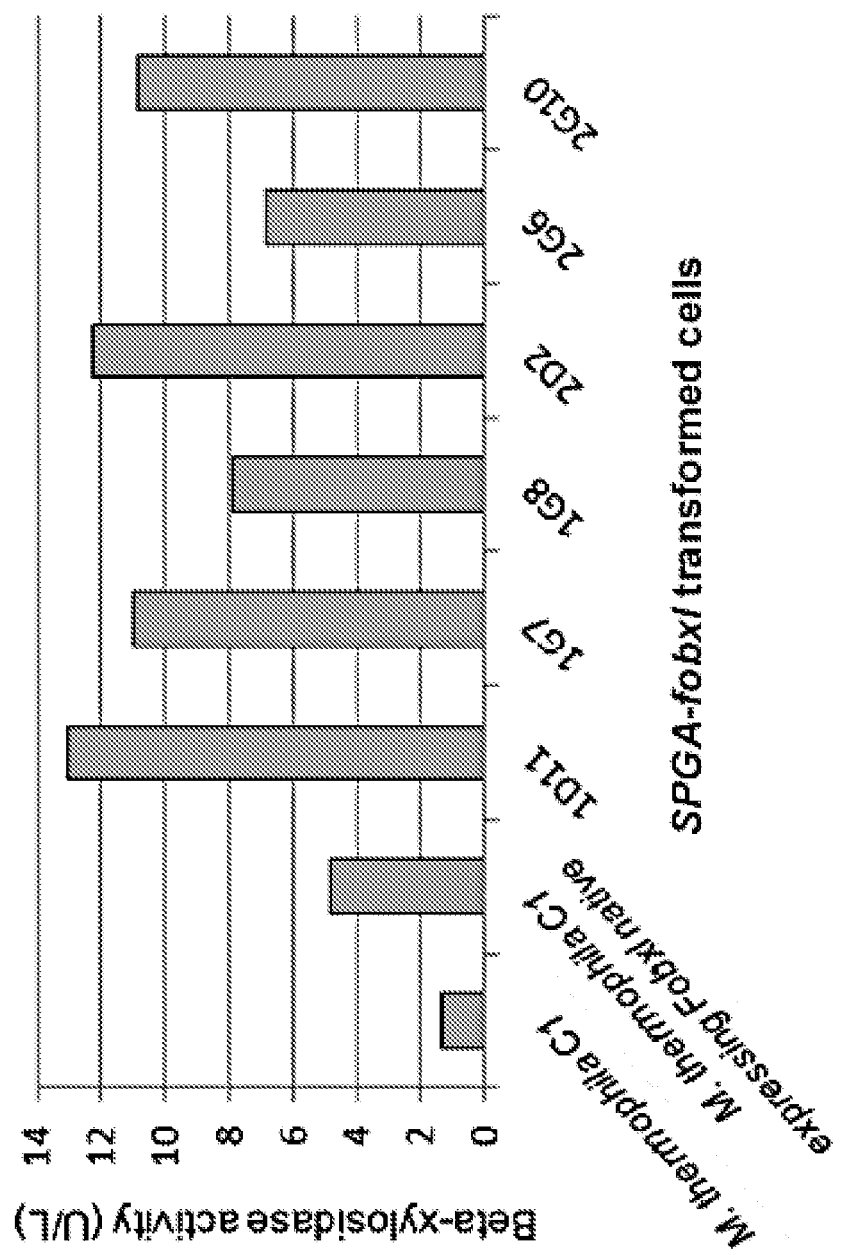
FIG. 6. Shows the beta-xylosidase activity (U/L) of some SPGA-fobxl transformants analysed using pNXP as substrate.

Among the transformants tested, most of them showed higher beta-xylosidase activity than the observed with the transformants expressing fobxl with native signal peptide. *M. thermophila* C1 was used as negative control. The results of beta-xylosidase activity are shown in FIG. 6. All the transformants with higher beta-xylosidase activity were confirmed in a second round test in MTPs and flask fermentation was performed as described in Example 1. Higher beta-xylosidase activity was confirmed in all of them.

Example 3. Beta-Xylosidase Activity Determination on Enzymatic Mixtures Produced by M. thermophila C1 and Transformants Expressing the FoBxl or SPGA-FoBxl Production of Enzymatic Cocktails Production of the enzyme cocktails was performed as described in Verdoes et al. (2007) and Visser et al., 2011, *Ind. Biotechnol.* 7 (3), using the industrial platform for the expression of industrial enzymes based on *M. thermophila* C1 developed by Dyadic Netherlands.

Three different enzymatic cocktails were produced: a control cocktail, the FoBxl cocktail and the SPGA-FoBxl cocktail. The control cocktail consisted of the mixture of extracellular enzymes produced by *Myceliophthora thermophila* C1 strain under the production conditions described in the references given above. The FoBxl and SPGA-FoBxl enzyme cocktails consisted of the mixtures of enzymes produced by this C1 strain successfully expressing respective constructions (described in examples 1 and 2) under identical production conditions.

Beta-Xylosidase Activity Determination

Beta-xylosidases (EC 3.2.1.27) are hydrolytic enzymes that catalyze the cleaving off the terminal xylose units from the non-reducing end of the short xylose oligomers arising from the endoxylanase (EC 3.2.1.8) activity towards xylan.

Beta-xylosidase activity was determined using p-nitrophenyl-beta-D-xylopyranoside (pNXP, Sigma N2132) as substrate. For this pNXP assay, the enzymatic reaction mixtures (1 mL final volume) containing 100 µmol sodium acetate buffer (pH 5.0), 100 µg pNXP (0.33 µmol) and proper amount of respective enzyme cocktail were incubated at 50° C. for 10 min. The amount of p-nitrophenol released was measured at $A_{410}$ ($\epsilon 410=15.2$ $mM^{-1}$ $cm^{-1}$) after addition of 100 µg sodium carbonate to the reaction mixtures. One unit of pNXP hydrolysing activity was defined as the amount of enzyme needed to release 1 µmol p-nitrophenol per minute. Obtained specific activities are shown in Table 1.

Total protein of the enzymatic mixtures was determined by the BCA method (Applichem, A7787 0500).

TABLE 1

Specific activity of enzymatic mixtures produced by *M. thermophila* C1 and transformants expressing the FoBxl or SPGA-FoBxl. Errors are indicated as the standard deviation (SD) of three independent measurements.

| Enzyme cocktail | BXL activity (U mg prot.$^{-1}$) | SD |
|---|---|---|
| Control cocktail | 11.47 | 0.04 |
| FoBxl cocktail | 36.05 | 0.19 |
| SPGA-FoBxl cocktail | 154.06 | 0.77 |

Example 4. Effect of FoBxl and SPGA-FoBxl Cocktail Supplementation on the Production of Xylose During the Enzymatic Hydrolysis of Xylan-Containing Biomass Enzymatic Hydrolysis Experiments Unwashed pretreated corn stover (PCS) was used as substrate for enzymatic hydrolysis. Pre-treatment of the biomass was performed by a modification of the steam explosion system described by Nguyen et al., 1998, *Appl. Biochem. Biotechnol.* 70-72, in which no acid treatment was applied so that xylan hydrolysis was impaired. Incomplete release of xylose from pre-treated material was necessary for the evaluation of the effect of the FoBxl and SPGA-FoBxl activities.

The compositional analysis of this material was performed accordingly to the Standard Biomass Analytical Procedures (http://www.nrel.gov/biomass/analytical_procedures.html), and revealed to contain a 4.06% and 11.11% (w/w, D.M.) of xylan and xylose concentration, respectively, and a 12.24% and 3.61% (w/w, DM) of glucan and glucose, respectively.

Hydrolysis reactions were performed in two phases. An initial phase was carried out by the control enzymatic cocktail during 24 hours at 25% dry matter (DM) concentration. This initial reaction mixture contained, in a total mass of 200 g: pretreated corn stover corresponding to 50 g DM; NaOH. 1.6 g; and control enzymatic cocktail with a content of 3 g of total protein (measured as previously described).

This initial hydrolysis phase was performed in 2 L ISO flasks to ensure liquefaction of the PCS; afterwards, resulting slurry was aliquoted into 10 mL tubes (4 g per tube), in which a second hydrolysis phase was performed.

Effect of FoBxl and SPGA-FoBxl was indeed studied during the second hydrolysis phase, in which 4 g of slurry were mixed with either 1 g of water (experimental control), or 1 g aqueous dilutions of corresponding cocktail. Therefore, DM of slurry was adjusted to 20% during this second phase of enzymatic hydrolysis, which was performed for 72 h. Enzymatic cocktail dosage was adjusted to 0.1% (w/w, protein/DM), the equivalent to 8 mg prot. g glucan$^{-1}$. Both phases of enzymatic hydrolysis were performed at 50° C. inside 25 mm orbit diameter shakers at 150 rpm.

Figure 7:
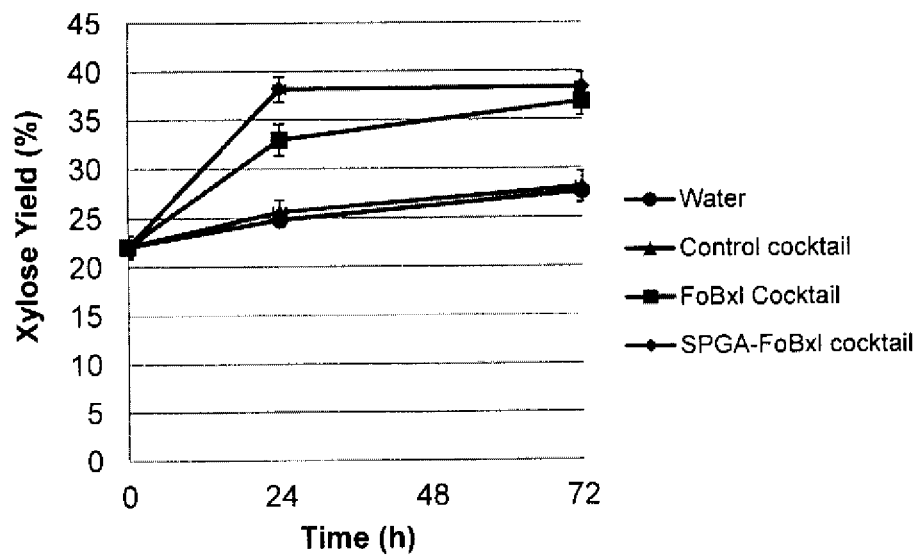
FIG. 7. Shows the xylose production profiles during the enzymatic hydrolysis of biomass by the enzymatic mixtures produced by *M. thermophila* C1 and transformants expressing the FoBxl or SPGA-FoBxl. Xylose yield is calculated as the percentage of xylose released compared to the maximum (%), according to the analysis of pre-treated material. Shown 72 h of process correspond to the phase 2 of enzymatic hydrolysis described in examples below. Data represent the average of three independent samples, and bars indicate the standard deviation.
Figure 8:
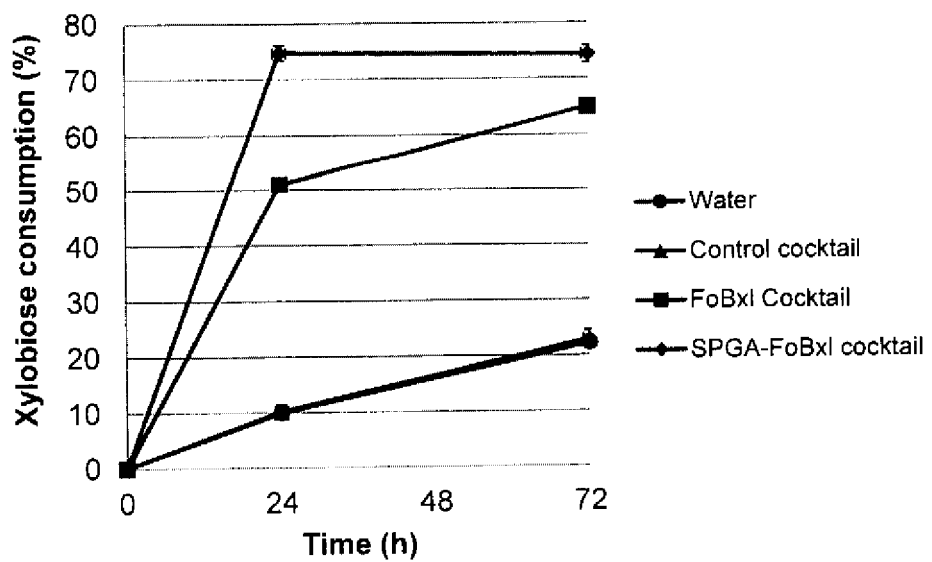
FIG. 8. Shows the xylobiose consumption profiles during the enzymatic hydrolysis of biomass by the enzymatic mixtures produced by *M. thermophila* C1 and transformants expressing the FoBxl or SPGA-FoBxl. Xylose consumption is calculated as the percentage of xylobiose hydrolysated from the initial value at the beginning of the enzymatic hydrolysis. Shown 72 h of process correspond to the phase 2 of enzymatic hydrolysis described in examples below. Data represent the average of three independent samples, and bars indicate the standard deviation.

Xylose production and xylobiose hydrolysis profiles obtained during this second phase of the enzymatic hydrolysis are shown in FIG. 7 and FIG. 8, wherein it can be seen that the use of cocktails obtained by transformants expressing FoBxl (SEQ ID NO: 3) or SPGA-FoBxl (SEQ ID NO: 4) leads to a great xylose and xylobiose production as compared with the control cocktail produced by the control (wild type) *Myceliophthora thermophila* C1 strain.

The invention claimed is:

1. A *Myceliophthora thermophila* host cell which expresses the recombinant beta-xylosidase enzyme which consists of the amino acid sequence SEQ ID NO: 4.

2. A composition comprising the host cell according to claim 1.

3. The composition according to claim 2, further comprising other cellulolytic enzymes expressed by a *Myceliophthora thermophila* host cell which expresses the recombinant beta-xylosidase enzyme which consists of the amino acid sequence SEQ ID NO: 4, wherein the cellulolytic enzymes are selected from the list consisting of: endoglucanases, beta-glucosidases, cellobiohydrolases, endoxylanases or any combination thereof.

4. A method of producing fermentable sugars comprising:
   a. Incubating biomass with the composition according to claim 2, and
   b. Recovering the fermentable sugars obtained after the incubation in step (a).

5. A method of producing a bioproduct from biomass comprising:
   a. Incubating biomass with the composition according to claim 2,
   b. Fermenting the fermentable sugars obtained after the incubation of step (a) with at least one fermenting microorganism, and
   c. Recovering the bioproduct obtained after the fermentation in step (b).

6. The method according to claim 5, wherein the bioproduct is biofuel.

7. The method according to claim 6, wherein the biofuel is bioethanol.

* * * * *

SEQUENCE LISTING

<160> NUMBER OF SEQ ID NOS: 8

<210> SEQ ID NO 1
<211> LENGTH: 1047
<212> TYPE: DNA
<213> ORGANISM: Artificial Sequence
<220> FEATURE:
<223> OTHER INFORMATION: Fobxl
<220> FEATURE:

```
<221> NAME/KEY: sig_peptide
<222> LOCATION: (1)..(60)

<400> SEQUENCE: 1
atgcagctca ggtttctgtc ttcagcattg ctgttgtctc tgaccagcaa atgcgctgcg      60
caaaacacta tgacattcc tccgctgatc accgacctct ggtccgcgga cccctcagct     120
catgttttcg aaggcaagct ctgggtttac ccatctcacg acatcgaagc caatgttgtc     180
aacggcacag gaggcgctca atacgccatg agggattacc ataccactc catgaagagc     240 atctatggta aagatcccgt tgtcgaccac ggcgtcgctc tctcagtcga tgacgttccc     300
tgggcgaagc agcaaatgtg gctcctgac gcagctcata agaacggcaa atattatctg     360
tacttccccg ccaaggacaa ggatgagatc ttcagaattg gagttgctgt ctccaacaag     420
cccagcggtc ctttcaaggc tgacaagagc tggattcctg gcacgtacag tatcgaccct     480
gctagctacg tcgacaatga taagaggcc tacctcatct ggggcggtat ctggggcggc     540
cagctccaag cctggcagga taaaagaac tttaacgagt cgtggatcgg agacaaggct     600
gctcctaacg gcaccaatgc cctatcccct cagatcgcca agctaagcaa ggacatgcac     660
aagatcaccg aaacaccccg cgatctcgtc attctcgccc ccgagacagg caagcctctt     720
caggctgagg acaacaagcg acgattcttc gagggccctt ggattcacaa gcgcggcaag     780
ctgtactacc tcatgtactc caccggtgat acccacttcc ttgtctacgc tacttccaag     840
aacatctacg gtccttatac ctaccagggc aagattcttg atcctgttga tgggtggact     900
actcatggaa gtattgttga gtataaggga cagtggtggc ttttctttgc tgatgcgcat     960
acgtctggta aggattacct tcgacaggtg aaggcgagga agatctggta tgacaagaac    1020
ggcaagatct tgcttcaccg tccttag                                       1047

<210> SEQ ID NO 2
<211> LENGTH: 348
<212> TYPE: PRT
<213> ORGANISM: Fusarium oxysporum
<220> FEATURE:
<221> NAME/KEY: SIGNAL
<222> LOCATION: (1)..(20)

<400> SEQUENCE: 2

Met Gln Leu Arg Phe Leu Ser Ser Ala Leu Leu Ser Leu Thr Ser
 1               5                  10                  15

Lys Cys Ala Ala Gln Asn Thr Asn Asp Ile Pro Pro Leu Ile Thr Asp
                20                  25                  30

Leu Trp Ser Ala Asp Pro Ser Ala His Val Phe Glu Gly Lys Leu Trp
             35                  40                  45

Val Tyr Pro Ser His Asp Ile Glu Ala Asn Val Val Asn Gly Thr Gly
         50                  55                  60

Gly Ala Gln Tyr Ala Met Arg Asp Tyr His Thr Tyr Ser Met Lys Ser
65                  70                  75                  80

Ile Tyr Gly Lys Asp Pro Val Val Asp His Gly Val Ala Leu Ser Val
                85                  90                  95

Asp Asp Val Pro Trp Ala Lys Gln Gln Met Trp Ala Pro Asp Ala Ala
            100                 105                 110

His Lys Asn Gly Lys Tyr Tyr Leu Tyr Phe Pro Ala Lys Asp Lys Asp
        115                 120                 125

Glu Ile Phe Arg Ile Gly Val Ala Val Ser Asn Lys Pro Ser Gly Pro
    130                 135                 140
```

-continued

```
Phe Lys Ala Asp Lys Ser Trp Ile Pro Gly Thr Tyr Ser Ile Asp Pro
145                 150                 155                 160

Ala Ser Tyr Val Asp Asn Asp Lys Glu Ala Tyr Leu Ile Trp Gly Gly
                165                 170                 175

Ile Trp Gly Gly Gln Leu Gln Ala Trp Gln Asp Lys Lys Asn Phe Asn
            180                 185                 190

Glu Ser Trp Ile Gly Asp Lys Ala Ala Pro Asn Gly Thr Asn Ala Leu
        195                 200                 205

Ser Pro Gln Ile Ala Lys Leu Ser Lys Asp Met His Lys Ile Thr Glu
    210                 215                 220

Thr Pro Arg Asp Leu Val Ile Leu Ala Pro Glu Thr Gly Lys Pro Leu
225                 230                 235                 240

Gln Ala Glu Asp Asn Lys Arg Arg Phe Phe Glu Gly Pro Trp Ile His
                245                 250                 255

Lys Arg Gly Lys Leu Tyr Tyr Leu Met Tyr Ser Thr Gly Asp Thr His
            260                 265                 270

Phe Leu Val Tyr Ala Thr Ser Lys Asn Ile Tyr Gly Pro Tyr Thr Tyr
        275                 280                 285

Gln Gly Lys Ile Leu Asp Pro Val Asp Gly Trp Thr Thr His Gly Ser
    290                 295                 300

Ile Val Glu Tyr Lys Gly Gln Trp Trp Leu Phe Phe Ala Asp Ala His
305                 310                 315                 320

Thr Ser Gly Lys Asp Tyr Leu Arg Gln Val Lys Ala Arg Lys Ile Trp
                325                 330                 335

Tyr Asp Lys Asn Gly Lys Ile Leu Leu His Arg Pro
            340                 345
```

<210> SEQ ID NO 3
<211> LENGTH: 328
<212> TYPE: PRT
<213> ORGANISM: Fusarium oxysporum

<400> SEQUENCE: 3

```
Gln Asn Thr Asn Asp Ile Pro Pro Leu Ile Thr Asp Leu Trp Ser Ala
1               5                   10                  15

Asp Pro Ser Ala His Val Phe Glu Gly Lys Leu Trp Val Tyr Pro Ser
                20                  25                  30

His Asp Ile Glu Ala Asn Val Val Asn Gly Thr Gly Gly Ala Gln Tyr
            35                  40                  45

Ala Met Arg Asp Tyr His Thr Tyr Ser Met Lys Ser Ile Tyr Gly Lys
        50                  55                  60

Asp Pro Val Val Asp His Gly Val Ala Leu Ser Val Asp Val Pro
65                  70                  75              80

Trp Ala Lys Gln Gln Met Trp Ala Pro Asp Ala His Lys Asn Gly
                85                  90                  95

Lys Tyr Tyr Leu Tyr Phe Pro Ala Lys Asp Lys Asp Glu Ile Phe Arg
            100                 105                 110

Ile Gly Val Ala Val Ser Asn Lys Pro Ser Gly Pro Phe Lys Ala Asp
        115                 120                 125

Lys Ser Trp Ile Pro Gly Thr Tyr Ser Ile Asp Pro Ala Ser Tyr Val
    130                 135                 140

Asp Asn Asp Lys Glu Ala Tyr Leu Ile Trp Gly Gly Ile Trp Gly Gly
145                 150                 155                 160

Gln Leu Gln Ala Trp Gln Asp Lys Lys Asn Phe Asn Glu Ser Trp Ile
                165                 170                 175
```

Gly Asp Lys Ala Ala Pro Asn Gly Thr Asn Ala Leu Ser Pro Gln Ile
            180                 185                 190

Ala Lys Leu Ser Lys Asp Met His Lys Ile Thr Glu Thr Pro Arg Asp
        195                 200                 205

Leu Val Ile Leu Ala Pro Glu Thr Gly Lys Pro Leu Gln Ala Glu Asp
    210                 215                 220

Asn Lys Arg Arg Phe Phe Glu Gly Pro Trp Ile His Lys Arg Gly Lys
225                 230                 235                 240

Leu Tyr Tyr Leu Met Tyr Ser Thr Gly Asp Thr His Phe Leu Val Tyr
                245                 250                 255

Ala Thr Ser Lys Asn Ile Tyr Gly Pro Tyr Thr Tyr Gln Gly Lys Ile
            260                 265                 270

Leu Asp Pro Val Asp Gly Trp Thr Thr His Gly Ser Ile Val Glu Tyr
        275                 280                 285

Lys Gly Gln Trp Trp Leu Phe Phe Ala Asp Ala His Thr Ser Gly Lys
    290                 295                 300

Asp Tyr Leu Arg Gln Val Lys Ala Arg Lys Ile Trp Tyr Asp Lys Asn
305                 310                 315                 320

Gly Lys Ile Leu Leu His Arg Pro
                325

<210> SEQ ID NO 4
<211> LENGTH: 346
<212> TYPE: PRT
<213> ORGANISM: Artificial Sequence
<220> FEATURE:
<223> OTHER INFORMATION: Aspergillus niger
<220> FEATURE:
<221> NAME/KEY: SIGNAL
<222> LOCATION: (1)..(18)

<400> SEQUENCE: 4

Met Ser Phe Arg Ser Leu Leu Ala Leu Ser Gly Leu Val Cys Ser Gly
1               5                   10                  15

Leu Ala Gln Asn Thr Asn Asp Ile Pro Pro Leu Ile Thr Asp Leu Trp
            20                  25                  30

Ser Ala Asp Pro Ser Ala His Val Phe Glu Gly Lys Leu Trp Val Tyr
        35                  40                  45

Pro Ser His Asp Ile Glu Ala Asn Val Val Asn Gly Thr Gly Gly Ala
    50                  55                  60

Gln Tyr Ala Met Arg Asp Tyr His Thr Tyr Ser Met Lys Ser Ile Tyr
65                  70                  75                  80

Gly Lys Asp Pro Val Val Asp His Gly Val Ala Leu Ser Val Asp Asp
                85                  90                  95

Val Pro Trp Ala Lys Gln Met Trp Ala Pro Asp Ala Ala His Lys
            100                 105                 110

Asn Gly Lys Tyr Tyr Leu Tyr Phe Pro Ala Lys Asp Lys Asp Glu Ile
        115                 120                 125

Phe Arg Ile Gly Val Ala Val Ser Asn Lys Pro Ser Gly Pro Phe Lys
    130                 135                 140

Ala Asp Lys Ser Trp Ile Pro Gly Thr Tyr Ser Ile Asp Pro Ala Ser
145                 150                 155                 160

Tyr Val Asp Asn Asp Lys Glu Ala Tyr Leu Ile Trp Gly Gly Ile Trp
                165                 170                 175

Gly Gly Gln Leu Gln Ala Trp Gln Asp Lys Lys Asn Phe Asn Glu Ser
            180                 185                 190

```
Trp Ile Gly Asp Lys Ala Ala Pro Asn Gly Thr Asn Ala Leu Ser Pro
            195                 200                 205

Gln Ile Ala Lys Leu Ser Lys Asp Met His Lys Ile Thr Glu Thr Pro
        210                 215                 220

Arg Asp Leu Val Ile Leu Ala Pro Glu Thr Gly Lys Pro Leu Gln Ala
225                 230                 235                 240

Glu Asp Asn Lys Arg Arg Phe Phe Glu Gly Pro Trp Ile His Lys Arg
                245                 250                 255

Gly Lys Leu Tyr Tyr Leu Met Tyr Ser Thr Gly Asp Thr His Phe Leu
            260                 265                 270

Val Tyr Ala Thr Ser Lys Asn Ile Tyr Gly Pro Tyr Thr Tyr Gln Gly
        275                 280                 285

Lys Ile Leu Asp Pro Val Asp Gly Trp Thr Thr His Gly Ser Ile Val
        290                 295                 300

Glu Tyr Lys Gly Gln Trp Trp Leu Phe Phe Ala Asp Ala His Thr Ser
305                 310                 315                 320

Gly Lys Asp Tyr Leu Arg Gln Val Lys Ala Arg Lys Ile Trp Tyr Asp
                325                 330                 335

Lys Asn Gly Lys Ile Leu Leu His Arg Pro
            340                 345

<210> SEQ ID NO 5
<211> LENGTH: 1041
<212> TYPE: DNA
<213> ORGANISM: Artificial Sequence
<220> FEATURE:
<223> OTHER INFORMATION: Synthetic Polypeptide
<220> FEATURE:
<221> NAME/KEY: sig_peptide
<222> LOCATION: (1)..(54)

<400> SEQUENCE: 5
atgtcgttcc gatctcttct cgccctgagc ggccttgtct gctcggggtt ggcacaaaac      60
actaatgaca ttcctccgct gatcaccgac ctctggtccg cggacccctc agctcatgtt     120
ttcgaaggca agctctgggt ttacccatct cacgacatcg aagccaatgt tgtcaacggc     180
acaggaggcg ctcaatacgc catgagggat taccatacct actccatgaa gagcatctat     240
ggtaaagatc ccgttgtcga ccacggcgtc gctctctcag tcgatgacgt tcctggggcg     300
aagcagcaaa tgtgggctcc tgacgcagct cataagaacg caaatatta tctgtacttc      360 cccgccaagg acaaggatga gatcttcaga attggagttg ctgtctccaa caagcccagc     420
ggtcctttca aggctgacaa gagctggatt cctggcacgt acagtatcga ccctgctagc     480
tacgtcgaca tgataaaga ggcctacctc atctggggcg gtatctgggg cggccagctc      540
caagcctggc aggataaaaa gaactttaac gagtcgtgga tcggagacaa ggctgctcct     600
aacggcacca tgccctatc ccctcagatc gccaagctaa gcaaggacat gcacaagatc      660
accgaaacac cccgcgatct cgtcattctc gccccgaga caggcaagcc tcttcaggct      720
gaggacaaca agcgacgatt cttcgagggc ccttggattc acaagcgcgg caagctgtac     780
tacctcatgt actccaccgg tgataccac ttccttgtct acgctacttc caagaacatc      840
tacggtcctt ataccacca gggcaagatt cttgatcctg ttgatgggtg gactactcat      900
ggaagtattg ttgagtataa gggacagtgg tggctttct ttgctgatgc gcatacgtct      960
ggtaaggatt accttcgaca ggtgaaggcg aggaagatct ggtatgacaa gaacggcaag    1020
atcttgcttc accgtcctta g                                              1041
```

<210> SEQ ID NO 6
<211> LENGTH: 987
<212> TYPE: DNA
<213> ORGANISM: Artificial Sequence
<220> FEATURE:
<223> OTHER INFORMATION: Synthetic Polypeptide

<400> SEQUENCE: 6

```
caaaacacta atgacattcc tccgctgatc accgacctct ggtccgcgga cccctcagct      60
catgttttcg aaggcaagct ctgggtttac ccatctcacg acatcgaagc caatgttgtc     120
aacggcacag gaggcgctca atacgccatg agggattacc ataccactc catgaagagc      180
atctatggta aagatcccgt tgtcgaccac ggcgtcgctc tctcagtcga tgacgttccc     240
tgggcgaagc agcaaatgtg ggctcctgac gcagctcata agaacggcaa atattatctg     300
tacttccccg ccaaggacaa ggatgagatc ttcagaattg gagttgctgt ctccaacaag     360
cccagcggtc ctttcaaggc tgacaagagc tggattcctg gcacgtacag tatcgaccct     420
gctagctacg tcgacaatga taaagaggcc tacctcatct ggggcggtat ctggggcggc     480
cagctccaag cctggcagga taaaaagaac tttaacgagt cgtggatcgg agacaaggct     540
gctcctaacg gcaccaatgc cctatcccct cagatcgcca agctaagcaa ggacatgcac     600
aagatcaccg aaacaccccg cgatctcgtc attctcgccc ccgagacagg caagcctctt     660
caggctgagg acaacaagcg acgattcttc gagggcccctt ggattcacaa gcgcggcaag     720
ctgtactacc tcatgtactc caccggtgat acccacttcc ttgtctacgc tacttccaag     780
aacatctacg gtccttatac ctaccagggc aagattcttg atcctgttga tgggtggact     840
actcatggaa gtattgttga gtataaggga cagtggtggc ttttctttgc tgatgcgcat     900
acgtctggta aggattacct tcgacaggtg aaggcgagga agatctggta tgacaagaac     960
ggcaagatct tgcttcaccg tccttag                                         987
```

<210> SEQ ID NO 7
<211> LENGTH: 105
<212> TYPE: DNA
<213> ORGANISM: Artificial Sequence
<220> FEATURE:
<223> OTHER INFORMATION: Glucoamylase signal peptide

<400> SEQUENCE: 7

```
gatcctcttc cgtcccatat gtcgttccga tctcttctcg ccctgagcgg ccttgtctgc      60
tcggggttgg cacaaaacac taatgacatt cctccgctga tcacc                    105
```

<210> SEQ ID NO 8
<211> LENGTH: 55
<212> TYPE: DNA
<213> ORGANISM: Artificial Sequence
<220> FEATURE:
<223> OTHER INFORMATION: Glucoamylase signal peptide

<400> SEQUENCE: 8

```
cctgcagccc gggggatccc taaggacggt gaagcaagat cttgccgttc ttgtc           55
```